United States Patent [19]

Naumann et al.

[11] Patent Number: 5,684,182

[45] Date of Patent: Nov. 4, 1997

[54] SULFONATED DIPHOSPHINES AND A PROCESS FOR THEIR PREPARATION

[75] Inventors: Christoph Naumann, Niedernhausen; Ahmed Tafesh, Kelkheim; Dieter Regnat, Eppstein; Hans-Jerg Kleiner, Kronberg, all of Germany

[73] Assignee: Hoechst Aktiengesellschaft, Germany

[21] Appl. No.: 604,573

[22] Filed: Feb. 21, 1996

[30] Foreign Application Priority Data

Feb. 23, 1995 [DE] Germany ............ 195 06 279.5

[51] Int. Cl.$^6$ .................................. C07C 309/35
[52] U.S. Cl. .................................. 562/35
[58] Field of Search .................................. 562/35

[56] References Cited

U.S. PATENT DOCUMENTS

| 5,274,183 | 12/1993 | Herrman et al. | 562/35 |
| 5,347,045 | 9/1994 | Herrmann et al. | 562/35 |
| 5,481,045 | 1/1996 | Herrmann et al. | 568/454 |

FOREIGN PATENT DOCUMENTS

| 0491240 | 6/1992 | European Pat. Off. |
| 0571819 | 1/1993 | European Pat. Off. |

*Primary Examiner*—Joseph Conrad
*Attorney, Agent, or Firm*—Connolly & Hutz

[57] ABSTRACT

The present invention relates to sulfonated diphosphines of the formula (I)

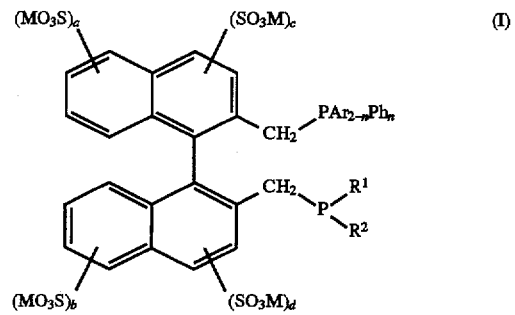

where M is hydrogen, ammonium, a monovalent metal or the equivalent of a polyvalent metal, a, b, c and d are each 0 or 1, with the proviso that a+b+c+d is an integer from 1 to 4, Ar is an m-$(MSO_3)$—$C_6H_4$ radical and M is as defined above, n is 0, 1 or 2, Ph is a phenyl radical, $R^1$ and $R^2$ are identical or different and are each an alkyl radical having from 1 to 10 carbon atoms or a cycloaliphatic radical having from 5 to 10 carbon atoms in the ring, and a process for their preparation.

21 Claims, No Drawings

SULFONATED DIPHOSPHINES AND A PROCESS FOR THEIR PREPARATION

The present invention relates to new compounds from the group consisting of sulfonated diphosphines and a process for their preparation.

Phosphines have found general, multifaceted, industrial use. They are suitable, for example, as antioxidants, metal extracts, flame inhibitors, stabilizers for olefins (U.S. Pat. No. 6,400,168 (NTIS); Chem. Abstr. 100; 122286b) and trioxane (U.S. Pat. No. 4,125,540), starting compounds for Wittig reagents or ligands for metal complex catalysts. Owing to their many forms, they also provide precursors for preparing further, optionally phosphorus-containing, organic compounds.

Within the group of phosphines, sulfonated diphosphines play a preeminent role because of their material properties. Since their molecule contains 2 trivalent phosphorus atoms, they have complexing properties towards numerous metals and metal ions, in particular those from the group consisting of the transition metals. The complex-forming capability is attributable to the formation of comparatively stable chelates and can be utilized for preparing corresponding metal complex catalysts which are used in industrial processes.

EP 0 571 819 A relates to sulfonated 2,2'-bis (diphenylphosphinomethyl)-1,1'-binaphthalenes of the formula (A)

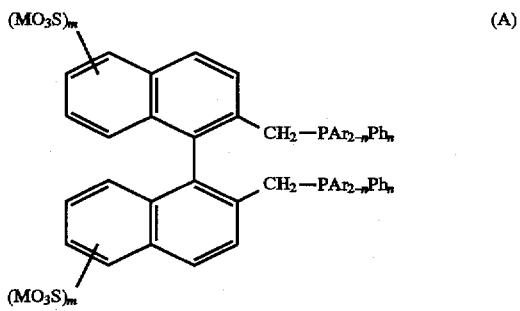

where Ar is m-$C_6H_4SO_3M$, M is hydrogen, ammonium, a monovalent metal or the equivalent of a polyvalent metal, Ph is a phenyl radical, m is 1 or 2 and n is 0, 1 or 2. These sulfonated diphosphines are used in combination with rhodium as hydroformylation catalysts. Owing to their water solubility, which is attributable to the incorporation of the sulfonic acid or sulfonate groups, these diphosphines open up the possibility of carrying out the hydroformylation in a heterogeneous phase. This process variant is particularly advantageous because it opens up a route for removing, simply and in a gentle manner, the catalyst dissolved in water from the water-insoluble reaction product.

In view of the particular importance which attaches to compounds from the group consisting of sulfonated diphosphines, it is a rewarding objective to provide new compounds from this group so as not only to supplement the spectrum of possible applications but also to enrich and expand the range by subtle changes in material properties and variation of structural features. It can be assumed that the chemical nature and the structural make-up of the sulfonated diphosphines exercises an influence on processes in which these sulfonated diphosphines are used as a catalyst constituent. In particular, it is an interesting challenge to combine the particular properties of symmetrically substituted, sulfonated diphosphines with the advantageous influences resulting from unsymmetric substitution and thus from static and/or electronic effects or chirality arising in addition, in such a way as to lead to new unsymmetrically sulfonated diphosphines which encompass an even larger or different type of application area than the symmetrically substituted, sulfonated diphosphines.

This object is achieved by sulfonated diphosphines of the formula (I)

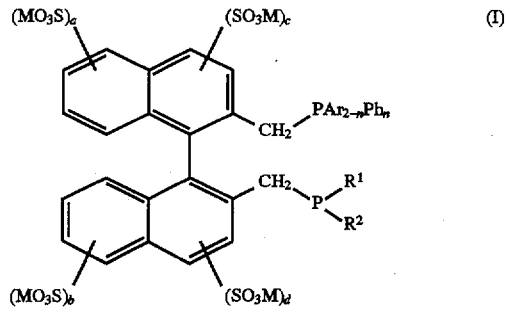

where M is hydrogen, ammonium, a monovalent metal or the equivalent of a polyvalent metal, a, b, c and d are each 0 or 1, with the proviso that a+b+c+d is an integer from 1 to 4, Ar is an m-$(MSO_3)$—$C_6H_4$ radical and M is as defined above, n is 0, 1 or 2, Ph is a phenyl radical, $R^1$ and $R^2$ are identical or different and are each an alkyl radical having from 1 to 10 carbon atoms or a cycloaliphatic radical having from 5 to 10 carbon atoms in the ring.

The sulfonated diphosphines of the formula (I) are interesting compounds owing to their chemical behavior which may also be attributable to the incorporation of two trivalent phosphorus atoms in the molecule and because of their particular structure. The particular structure of the diphosphines is due, on the one hand, to the 2,2'-dimethyl-1,1'-binaphthyl radical and, on the other hand, to the two differently substituted phosphorus atoms. The two differently substituted phosphorus atoms lead to the diphosphines of the formula (I) being unsymmetrically substituted compounds.

The sulfonated diphosphines of the formula (I) are sulfonated 2-(diphenylphosphinomethyl)-2'-(dialkylphosphinomethyl)-1,1'-binaphthalenes or sulfonated 2-(diphenylphosphinomethyl)-2'-(dicycloalkylphosphinomethyl)-1,1'-binaphthalenes or sulfonated 2-(diphenylphosphinomethyl)-2'-(alkylcycloalkylphosphino)-1,1'-binaphthalenes.

Owing to their sulfonic acid or sulfonate groups, they are water-soluble compounds and are thus suitable for carrying out a reaction in a heterogeneous phase. This process variant is particularly advantageous since it opens up a route for separating, simply and in a gentle manner, a catalyst dissolved in water from the water-insoluble reaction products.

The sulfonated diphosphines contain, depending on the degree of sulfonation, up to 6 sulfonic acid or sulfonate groups. Their solubility in water rises with the degree of sulfonation.

The invention provides sulfonated diphosphines of the formula (I), where M is hydrogen or an alkali metal ion, in particular hydrogen $Na^+$ or $K^+$, preferably $Na^+$.

Depending on the degree of sulfonation, a+b+c+d is, in particular, an integer from 2 to 4.

n can be 0 or 1, but also 2.

The radicals $R^1$ and $R^2$ are identical or different and are each an alkyl radical having from 1 to 6, in particular from 1 to 4, carbon atoms or a cycloaliphatic radical having 5 or 6, in particular 6, carbon atoms in the ring.

Of particular interest are the sulfonated diphosphines in which $R^1$ and $R^2$ are identical, since they are usually more easily obtainable than the sulfonated disphosphines in which $R^1$ and $R^2$ are different from one another. These include, in particular, the sulfonated diphosphines in which $R^1$ and $R^2$ are each a cyclohexyl radical.

The present invention further provides a process for preparing the sulfonated diphosphines of the formula (I). It comprises sulfonating a diphosphine of the formula (II)

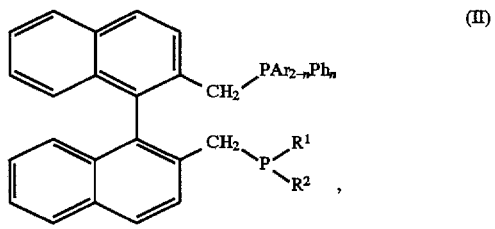

(II)

where Ar, n, Ph, $R^1$ and $R^2$ are as defined for the formula (I) above, with oleum at temperatures of from 0° to 25° C., hydrolyzing the sulfonation mixture and isolating the sulfonated diphosphines of the formula (I) from the sulfonated hydrolysis mixture.

Of particular importance are the diphosphines of the formula (II) in which n=2. These diphosphines are prepared starting out from a 2-(diphenylphosphinomethyl)-2'-(dialkylphosphinomethyl)-1,1'-binaphthalene or from 2-(diphenylphosphinomethyl)-2'-(dicycloalkylphosphinomethyl)-1,1'-binaphthalene as base molecule. These compounds are obtained via a multistage synthesis by reductive dimerization of 1-bromo-2-methylnaphthalene, reaction of the binaphthalene formed therefrom with N-bromosuccinimide, with 2,2'-bis(bromomethyl)-1,1'-binaphthalene being formed. The reaction of this dibromo compound, for example with a dialkylphosphlne or with a cyclohexylphosphine gives the corresponding phosphepinium bromides. Such phosphepinium bromides and their preparation are subject matter of a German Patent Application (number P 44 19 990.2) which is not a prior publication.

The phosphepinium bromides can undergo a nucleophilic ring opening on reaction with potassium diphenylphosphide to give the corresponding 2-(diphenylphosphinomethyl)-2'-(dialkylphosphinomethyl)-1,1'-binaphthalenes or 2-(diphenylphosphinomethyl)-2'-(dicycloalkylphosphinomethyl)-1,1'-binaphthalenes. Such diphosphines of the formula (II) and their preparation are subject matter of a German Patent Application (number P 44 34 844.4) which is not a prior publication.

To introduce the sulfonic acid groups into the binaphthyl radical and into the phenyl radicals, the diphosphine of the formula (II) is treated with excess sulfur trioxide in the form of oleum as sulfonating agent. Concentrated sulfuric acid has been found to be useful as solvent for the diphosphine to be sulfonated. The solution consisting of the diphosphine and sulfuric acid can be introduced in portions into oleum or can be admixed with portions of oleum. It is advisable to stir the reaction mixture vigorously, cool it well and to combine the reactants slowly and in small portions so that the heat of reaction can easily be dissipated. This prevents the sulfonation from proceeding in an uncontrolled manner, but instead $SO_3H$ groups are introduced successively into the binaphthyl radical and the phenyl radicals. In addition, oxidation of the phosphorus is effectively suppressed. After addition of the entire sulfonating agent or diphosphine, the subsequent reaction can be carried out at room temperature, i.e. at from about 20° to 25° C., essentially without external cooling. However, it is advantageous to stir the reaction mixture in this stage too, so as to uniformly distribute any heat of reaction still being evolved and to be able to dissipate it without delay.

Decisive factors for the achievable degree of sulfonation are, in particular, the $SO_3$ concentration in the oleum, the reaction temperature and the reaction time. The specified parameters influence one another.

It has been found useful to use oleum containing from 10 to 65, or even more, % by weight, in particular from 40 to 65% by weight, of free sulfur trioxide.

The reaction temperature is, as already mentioned above, from 0° to 25° C., in particular from 0° to 20° C., preferably from 0° to 10° C.

The sulfonating agent is to be used in excess, based on the diphosphine of the formula (I). Advantageously, from 25 to 80 mol, in particular from 40 to 70 mol, of sulfur trioxide are used per mole of diphosphine of the formula (II). Oleum containing free $SO_3$ in high concentration, i.e. in a proportion of from about 40 to 65 and more % by weight of sulfur trioxide, leads to products which contain at least 4 $SO_3H$ groups and as a result are very readily soluble in water. Concentrations of free $SO_3$ in oleum which are lower than about 40% by weight give products having a lower degree of sulfonation, i.e. diphosphines having a lower solubility in water are formed.

In principle, it is also possible to use higher $SO_3$ concentrations, but they generally favor the oxidation of the diphosphines to form phosphine oxides substantially more strongly than the sulfonation so that overall the yield of sulfonated diphosphines decreases. For the same reason, it is also not advisable to compensate for low concentrations of free $SO_3$ by increasing the reaction temperature.

In contrast, the degree of sulfonation of the diphosphine can be successfully influenced by means of the reaction time. Longer reaction times lead to more highly sulfonated compounds than do shorter reaction times. In general, the reaction in the specified temperature ranges requires from 10 to 60 hours, in particular from 15 to 48 hours. This reaction time applies, in particular, when using oleum containing about 40 and more % by weight of free sulfur trioxide. Oleum of lower concentration leads, even with long reaction times, to compounds which are only partially sulfonated, with the increasing formation of oxidation products not being able to be completely avoided.

The sulfonation is therefore advantageously carried out using relatively highly concentrated oleum and the degree of sulfonation is controlled via the reaction time.

Subsequent to the sulfonation, the reaction mixture is hydrolyzed. In this process step care has to be taken to ensure that a temperature of about 30° C. is not exceeded. It is advantageous to carry out the hydrolysis at a temperature of from 0° to 25° C., in particular from 15° to 25° C. It is therefore advisable to carefully pour the reaction mixture onto ice or to carry out the hydrolysis using ice water and to provide intensive external cooling.

The diluted solution containing essentially the different sulfonation stages of the diphosphine of the formula (I) and sulfuric acid is worked up in further process steps.

For this purpose, the sulfuric acid solution is neutralized, i.e. the hydrolyzed sulfonation mixture is reacted with an alkaline reagent such as an alkali metal carbonate or alkali metal hydroxide, the alkali metal sulfate is separated off, the solution is evaporated and the sulfonated diphosphines of the formula (I) are extracted from the residue using a mixture of alcohols having up to 5 carbon atoms and water.

So as not to increase unnecessarily the volume of the reaction mixture and to substantially precipitate the alkali metal sulfate which forms, the neutralizing agent is used as a highly concentrated solution or in undissolved solid form, for example sodium hydroxide flakes, sodium hydroxide pellets.

Owing to its low solubility at low temperatures, the major part of the alkali metal sulfate can be removed from the solution by cooling. The temperatures suitable for this purpose are a function of the concentration of the sulfate in the solution and the temperature dependence of its solubility. The most favorable conditions are therefore to be determined experimentally from case to case. The sulfate removal can be carried out in one or more stages. It has been found to be advantageous to carry out the crystallization in two stages.

After precipitation of the alkali metal sulfate, the solution is evaporated to dryness, preferably under reduced pressure, and diphosphines of different degrees of sulfonation are extracted in the form of their alkali metal salts from the crystal slurry. Suitable extractants are, for example, mixtures of lower alcohols, i.e. alcohols having up to 5 carbon atoms in the molecule, such as methanol, ethanol or propanol, with water. The extraction is carried out by customary methods in one or more stages, in particular from 2 to 4 stages. The extracts are combined and evaporated to dryness.

It has also been found to be useful to react the sulfuric acid solution, i.e. the hydrolyzed sulfonation mixture, with a mixture of a water-insoluble amine and an organic solvent and to extract the sulfonates as amine salts. Suitable amines are ones containing from 10 to 60, in particular from 13 to 36, carbon atoms, for example methyldioctylamine, tri-n-octylamine, triisooctylamine, tri-2-ethylhexylamine, tridodecylamine, in particular trioctylamine. Organic solvents which are successfully used are aliphatic and aromatic hydrocarbons or hydrocarbon mixtures, for example toluene or kerosine-like mixtures, in particular toluene.

From 0.5 to 1.5 mol, in particular from 0.8 to 1.2 mol, of amine is used per equivalent of sulfonic acid. After intensively mixing the sulfuric acid solution and the solution of the amine, aqueous and organic phases are separated from one another. The organic phase containing the amine salts of the sulfonated diphosphines is reacted with the solution of a base in water. Examples of particularly suitable bases are sodium hydroxide and potassium hydroxide. This gives an aqueous solution from which the corresponding alkali metal salt of the sulfonic acids can be isolated. An interesting process variant is not to add the base dissolved in water all at once to the solution of the amine salt in the organic medium, but to add it in portions.

Such gradated treatment of the amine solution, for example by setting certain pH values or pH ranges by means of the base, makes possible substantial removal of phosphine oxides from the sulfonation mixture and at the same time the partial fractionation of the sulfonation mixture into products of various sulfonation stages. The new sulfonated diphosphines of the formula (I) are solids. Depending on the sulfonation conditions, they contain up to 6 sulfonic acid groups. The alkali metal salts are soluble in water and their solubility increases with the degree of sulfonation.

Treatment of aqueous alkali metal salt solutions of the sulfonated diphosphines with a cation exchanger in the H$^+$ form enables the free acids to be prepared. Further salts of the new sulfonated diphosphines can be obtained from the acids by reaction with bases, for example hydroxides, carbonates, ammonia or amines.

The new compounds of the formula (I) have been found to be particularly good as components of catalysts for the reduction of aromatic nitro groups. This reaction is the subject matter of a German Patent Application (number 195 06 278.7) filed on the same day as the present invention.

As shown by the examples 5a, 5b and 5c of that application, the compounds of the formula (I) (see Example 5c) lead to significantly higher yields than known water-soluble phosphines (Examples 5a and 5b).

It is not necessary to use the sulfonated diphosphines as uniform compounds. It is also possible to use different sulfonation stages of the diphosphines and/or sulfonate mixtures with various cations.

The following examples illustrate the invention without limiting it.

EXPERIMENTAL PART

Example 1

2.0 g (3.02 mmol) of 2-(diphenylphosphinomethyl)-2'-(dicyclohexylphosphinomethyl)-1,1'-binaphthyl* are dissolved at from 0° to 10° C. in 7 ml of 96% strength sulfuric acid, admixed with 12.5 ml of 65% strength oleum while maintaining a temperature of from 3° to 7° C. and then stirred for 22 hours at room temperature. Subsequently, 82 ml of water are added dropwise to the sulfonation mixture at from 0° to 5° C. over a period of about 30 minutes. To separate the sulfonation product from the aqueous phase, the latter is extracted for 2 hours at room temperature with a solution of 10.5 ml of triisooctylamine in 40 ml of toluene. The aqueous phase is separated off and discarded. Subsequently, the organic phase is extracted at room temperature by addition of 3% strength by weight sodium hydroxide solution in three steps. At a pH of from 1.1 to 3.8, 30 ml of an aqueous phase are formed (reextract 1, containing sulfate). In the pH range from 3.8 to 6, 30 ml of an aqueous phase are formed (reextract 2). In the range from pH 6 to 12.5, the desired product fraction is separated off, with 25 ml of an aqueous solution being obtained (reextract 3).

*prepared as described in Example 2 of the German Patent Application (number P 44 34 844.4) which is not a prior publication.

Analytical Parameters of Reextracts 2 and 3

Reextract 2:

$^{31}$P-NMR spectrum (H$_2$O, pH 3.6 to 6) $\delta^{31}$P [P(Ar)$_2$P] (III): −11.4; −10.1; −9.2 ppm (48%) $\delta^{31}$P [P(O)(cyclohexyl)$_2$]P(V): +23.1; +25.2 (47%)

Reextract 3:

$^{31}$P-NMR spectrum (H$_2$O, pH 6 to 12.5) $\delta^{31}$P [P(Ar)$_2$]P(III): −11.3; −10.5; −10.1; −9.4 ppm (48%) $\delta^{31}$P [P(cyclohexyl)$_2$] P(III): +3.6; +4.2; +4.5; +4.9 ppm (51%)

Example 2

2.0 g (3.02 mmol) of 2-(diphenylphosphinomethyl)-2'-(dicyclohexylphosphinomethyl)-1,1'-binaphthyl are reacted using a method similar to Example 1, with 25 ml of an aqueous solution (reextract 3) being obtained. This aqueous solution (reextract 3) separated off in the pH range from 6 to 12.5 and containing the desired product fraction is evaporated to 10 ml at 10$^{-2}$ torr/80° C. 80 ml of acetone are subsequently added, giving a brown oil. The supernatant solution is decanted off, the residue is dissolved in a small amount of methanol (about 3 ml) and is reprecipitated by addition of 30 ml of ethanol. The solid obtained is filtered off and washed in succession with ethanol, acetone and petroleum ether (40°–60° C., low-boiling) and is dried. This gives a brown powder.

Yield: 780 mg Melting point: >230° C. $^1$H-NMR spectrum: (D$_2$O) δ=0.43–1.87 (m, cycloaliphatic H); 2.25–2.87 (m-CH$_2$—P(cyclohexyl)$_2$), 3.43–3.84 (m, —CH$_2$—P(Ar)$_2$); 7.0–8.85 (m, aryl-H). $^{31}$P-NMR spectrum: (D$_2$O) $\delta^{31}$P [P(Ar)$_2$P] (III): −11.9; −11.2; −10.2; −9.6 ppm (48%) $\delta^{31}$P [P(cyclohexyl)$_2$] P(III): +3.6; +3.9; +4.3; +4.6 ppm (47%) Mass spectrum: M$^+$=947 (20%), 969 (20%), 1027 (60%), 1049 (100%), 1071 (50%), 1142 (20%), 1151 (20%), 1173 (10%).

Example 3

2.0 g (3.02 mmol) of 2-(diphenylphosphinomethyl)-2'-(dicyclohexylphosphinomethyl)-1,1'-binaphthyl are reacted using a method similar to Example 1. The reaction time is 22 hours. To separate the sulfonation product from the aqueous phase, the latter is extracted for 1 hour at room temperature with a solution of 26.3 ml of triisooctylamine in 100 ml of toluene. The aqueous phase is discarded. Subsequently, the organic phase is extracted at room temperature by addition of 3% strength by weight sodium hydroxide solution in three steps. Up to a pH of 3, 30 ml of an aqueous phase are formed (reextract 1, sulfate). In the pH range from 3 to 6, 55 ml of an aqueous phase are formed (reextract 2). In the pH range from 6 to 13, the desired product is separated off, with 40 ml of an aqueous solution being obtained (reextract 3).

Analytical Parameters of Reextracts 2 and 3

Reextract 2:

$^{31}$P-NMR spectrum (H$_2$O, pH 3 to 6) $\delta^{31}$P [P(Ar)$_2$] (III): −10.0 ppm (20%) $\delta^{31}$P [P(O)(Ar)$_2$]+[P(O)(cyclohexyl)$_2$]P (V): +25; +34, +57 ppm (80%) Total content 3.1 g Melting point: >230° C.

Reextract 3: (desired product)

$^{31}$P-NMR spectrum (H$_2$O, pH 6 to 13) $\delta^{31}$P [P(Ar)$_2$] P(III): −11.4; −9.5; −9.0 ppm (48% of the intensity) $\delta^{31}$P [P(cyclohexyl)$_2$] P(III): +3.8; +4.3; +4.9 ppm (47% of the intensity) Total content: 4.8 g Melting point: >230° C. Mass spectrum: M$^+$=969 (25%), 1049 (60%), 1071 (100%), 1093 (80%), 1173 (20%). Elemental analysis: 13.0% by weight of sulfur; 5.2% by weight of phosphorus; 9.1% by weight of sodium This gives the following molar ratios:

P:S=1:2.5, P:Na=1:2.5 S:Na=1:1; corresponding to the introduction of five SO$_3$H groups into the 2-(diphenylphosphinomethyl)-2'-(dicyclohexylphosphinomethyl)-1,1'-binaphthalene molecule.

Example 4

15.0 g (22.6 mmol) of 2-(diphenylphosphinomethyl)-2'-(dicyclohexylphosphinomethyl)-1,1'-binaphthyl are dissolved at from 0° to 10° C. in 72.7 g of 96% strength sulfuric acid, admixed with 145.9 g of 65% strength oleum while maintaining a temperature of from 3° to 7° C. and then stirred for 48 hours at room temperature. For the hydrolysis, the sulfonation mixture is added dropwise to 400 ml of water at a temperature below 10° C. To separate the sulfonation product from the aqueous phase, the latter is extracted for 1 hour at 40° C. with a solution of 57.6 g of triisooctylamine in 150 ml of toluene. Subsequently, the organic phase is extracted at room temperature by addition of the 3% strength by weight sodium hydroxide solution in three steps. Up to a pH of 3, 300 ml of an aqueous phase are formed (reextract 1). This fraction consists mostly of sulfate and can be discarded. In the pH range from 3 to 6, 100 ml of an aqueous phase are formed (reextract 2). In the pH range from 6 to 12, the desired product is separated off, with 70 ml of an aqueous solution being obtained (reextract 3).

Analytical Parameters of Reextracts 2 and 3

Reextract 2:

$^{31}$P-NMR spectrum (H$_2$O, pH 3 to 6) $\delta^{31}$P [P(Ar)$_2$] P(III): −12.3; −11.8; −9.7; −8.9 ppm (35%) $\delta^{31}$P [P(O)(Ar)$_2$]+[P(O)(cyclohexyl)$_2$] P(V): +20.2; +57.8 ppm (56%) Total content 6.9 g Melting point: >230° C.

Reextract 3:

$^{31}$P-NMR spectrum (H$_2$O; pH 6 to 12) $\delta^{31}$P [P(Ar)$_2$]P (III): −11.8; −11.6; −11.0; −10.9; −10.4; −9.1 (47%) $\delta^{31}$P [P(cyclohexyl)$_2$] P(III): +3.7; +4.0; +4.2; +4.9; +5.7 (48%) Total content: 11.2 g Melting point: >230° C. $^1$H-NMR spectrum: (D$_2$O) $\delta$=0.43–1.88 (m, cycloaliphatics); 2.58–2.82 (m, —CH$_2$—P(cyclohexyl)$_2$); 3.35–3.70 (m, —CH$_2$—P(Ar)$_2$); 6.76–8.94 (m, aryl-H). $^{31}$P-NMR spectrum: (D$_2$O) $\delta^{31}$P[P(Ar)$_2$] P(III): −11.7; −11.3; −10.7; −10.3; −9.3 ppm (48%) $\delta^{31}$P[P(cyclohexyl)$_2$] P(III): +3.7; +4.3; +4.6 ppm (48%) Mass spectrum: M$^+$=923 (50%); 945 (50%); 1003 (80%); 1025 (100%) Elemental analysis: 12.4% by weight of sulfur; 4.3% by weight of phosphorus; 9.9% by weight of sodium This gives the following molar ratios:

P:S=1:3 P:Na=1:3 S:Na=1:1 corresponding to introduction of six SO$_3$H groups into the 2-(diphenylphosphinomethyl)-2'-(dicyclohexylphosphinomethyl)-1,1'-binaphthalene molecule.

Example 5

2.28 g (3.4 mmol) of 2-(diphenylphosphinomethyl)-2'-(dicyclohexylphosphinomethyl)-1,1'-binaphthyl are dissolved at from 0° to 10° C. in 8 ml of 96% strength sulfuric acid, admixed with 14.3 ml of 65% strength oleum while maintaining a temperature of from 3° to 7° C. and then stirred for 2 hours at room temperature. Subsequently, the sulfonation mixture is added dropwise over a period of 30 minutes to 94 ml of water (O$_2$-free) at below 10° C. To separate the sulfonation product from the aqueous phase, the latter is extracted for 1 hour at room temperature with a solution of 12 ml of triisooctylamine (TIOA) in 47 ml of toluene. The aqueous phase is discarded. The organic phase is subsequently extracted at room temperature by addition of 3% strength by weight sodium hydroxide solution in two stages. Up to a pH of 3, 50 ml of an aqueous phase are formed (reextract 1, sulfate). In the pH range from 3 to 7, 34 ml of an aqueous phase are formed (reextract 2, desired product). Reextract 3 is omitted.

Analytic Parameters of Reextract 2

Total content: 1.40 g Melting point: >230° C. Mass spectrum: M$^+$=925 (40%), 947 (50%), 969 (40%), 1003 (30%), 1027 (60%), 1049 (80%), 1071 (40%) $^1$H-NMR spectrum: (D$_2$O) $\delta$=0.35–1.94 (m, cycloaliphatics); 2.35–2.70 (m, —CH$_2$—P(cyclohexyl)$_2$); 3.40–3.58 (m, —CH$_2$—P(Ar)$_2$); 6.82–8.88 (m, aryl-H). $^{31}$P-NMR spectrum: (D$_2$O) $\delta^{31}$P[P(Ar)$_2$] P(III): −11.5; −10.5; −9.50 ppm (45%) $\delta^{31}$P[P(cyclohexyl)$_2$] P(III): +2.0; +6.5 ppm (42%)

Example 6

The procedure is as described in Example 5, but the reaction time is 7 hours. Up to a pH of 3, 60 ml of an aqueous phase are formed (reextract 1, sulfate). In the pH range from 3 to 7, 35 ml of an aqueous phase are formed (reextract 2, desired product). Reextract 3 is omitted.

Analytic Parameters of Reextract 2

$^{31}$P-NMR spectrum (H$_2$O, pH 3 to 7) $\delta^{31}$P [P(Ar)$_2$] P(III): −11.5; −10.5; −9.50 ppm (45%) $\delta^{31}$P[P(cyclohexyl$_2$)] P(III): +2.0; +6.5 ppm (42%) Total content: 2.0 g Melting point: >230° C. Mass spectrum: M$^+$=925 (40%), 947 (60%), 969 (65%), 991 (20%), 1003 (20%), 1031 (60%), 1049 (100%), 1071 (80%), 1093 (20%)

Example 7

The procedure is as described in Example 5, but the reaction time is 72 hours. Up to a pH of 3, 75 ml of an aqueous phase are formed (reextract 1, sulfate). In the pH range from 3 to 5.5, 17 ml of an aqueous phase are formed (reextract 2). In the pH range from 5.5 to 12, the desired product is separated off, with 33 ml of an aqueous solution being obtained (reextract 3).

Analytical Parameters of Reextracts 2 and 3

Reextract 2:

$^{31}$P-NMR spectrum (H$_2$O, pH 3 to 5.5) δ$^{31}$P P(III): −12.0; −11.6; −9.6 ppm (35%) δ$^{31}$P P(V): +33.2; +57.2 ppm (56%) Total content: 1.10 g Melting point: >230° C.

Reextract 3:

$^1$H-NMR spectrum: (D$_2$O) δ=0.41–1.88 (m, cycloaliphatics); 2.23–2.64 (m, —CH$_2$—P(cyclohexyl)$_2$); 3.35–3.76 (m, —CH$_2$—P(Ar)$_2$); 6.82–8.88 (m, aryl-H). $^{31}$P-NMR spectrum: (D$_2$O) δ$^{31}$P[P(Ar)$_2$] P(III): −11.6; −10.4; −9.2; −8.4 ppm (40%) δ$^{31}$P[P(cyclohexyl)$_2$] P(III): +4.0; +4.4; +5.2 ppm (32%) Total content: 1.75 Melting point: >230° C. Mass spectrum: M$^+$=961 (40%), 1003 (60%); 1025 (100%)

We claim:

1. A sulfonated diphosphine of the formula (I)

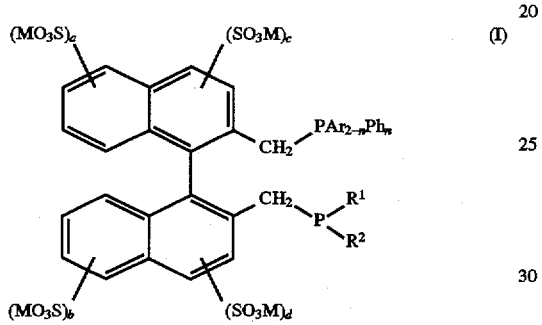

where M is hydrogen, ammonium, a monovalent metal or the equivalent of a polyvalent metal, a, b, c and d are each 0 or 1, with the proviso that a+b+c+d is an integer from 1 to 4, Ar is an m-(MSO$_3$)—C$_6$H$_4$ radical and M is as defined above, n is 0, 1 or 2, Ph is a phenyl radical, R$^1$ and R$^2$ are identical or different and are each an alkyl radical having from 1 to 10 carbon atoms or a cycloaliphatic radical having from 5 to 10 carbon atoms in the ring.

2. A sulfonated diphosphine as claimed in claim 1, wherein M is hydrogen or an alkali metal ion.

3. A sulfonated diphosphine as claimed in claim 1, wherein M is hydrogen, Na$^+$ or K$^+$.

4. A sulfonated diphosphine as claimed in claim 1, wherein M is Na$^+$.

5. A sulfonated diphosphine as claimed in claim 1, wherein a+b+c+d is an integer from 2 to 4.

6. A sulfonated diphosphine as claimed in claim 1, wherein n is 0 or 1.

7. A sulfonated diphosphine as claimed in claim 1, wherein n is 2.

8. A sulfonated diphosphine as claimed in claim 1, wherein R$^1$ and R$^2$ are each an alkyl radical having from 1 to 6 carbon atoms.

9. A sulfonated diphosphine as claimed in claim 1, wherein R$^1$ and R$^2$ are each a cycloaliphatic radical having from 5 to 6 carbon atoms in the ring.

10. A process for preparing sulfonated diphosphines as claimed in claim 1, which comprises sulfonating a diphosphine of the formula (II)

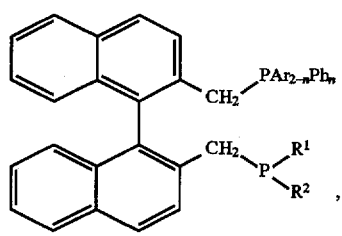

where Ar, n, Ph, R$^1$ and R$^2$ are as defined above, with oleum at temperatures of from 0° to 25° C., hydrolyzing the sulfonation mixture and isolating the sulfonated diphosphines of the formula (I) from the hydrolyzed sulfonation mixture.

11. The process as claimed in claim 10, wherein the diphosphine of the formula (II) which is used has n=2.

12. The process as claimed in claim 10, wherein the oleum used for the sulfonation contains from 10 to 65, % by weight of free sulfur trioxide.

13. The process as claimed in claim 10, wherein from 25 to 80 mol, of sulfur trioxide are used per mole of diphosphine of the formula (II).

14. The process as claimed in claim 10, wherein the sulfonation is carried out at temperatures of from 0° to 20° C.

15. The process as claimed in claim 10, wherein the hydrolysis of the sulfonation mixture is carried out at temperatures up to about 30° C.

16. The process as claimed in claim 10, wherein the hydrolyzed sulfonation mixture is neutralized with alkali metal carbonate or alkali metal hydroxide, alkali metal sulfate is separated off, the aqueous solution is evaporated and the sulfonated diphosphines of the formula (I) are extracted from the residue using a mixture of alcohols having up to 5 carbon atoms in the molecule and water.

17. The process as claimed in claim 10, wherein the hydrolyzed sulfonation mixture is reacted with a mixture of a water-insoluble amine and an organic solvent, in particular a mixture of triisooctylamine and toluene, the sulfonates are extracted as amine salts and the solution of the amine salts is admixed with a solution of a base, preferably sodium hydroxide or potassium hydroxide in water, if desired in portions.

18. The process as claimed in claim 10, wherein the oleum used for the sulfonation contains from 40 to 65% by weight of free sulfur trioxide.

19. The process as claimed in claim 10, wherein from 40 to 70 mol of sulfur trioxide are used per mole of diphosphine of the formula (II).

20. The process as claimed in claim 10, wherein the sulfonation is carded out at a temperature of from 0° to 10° C.

21. The process as claimed in claim 10, wherein the hydrolysis of the sulfonation mixture is carried out at a temperature of from 0° to 25° C.

* * * * *